United States Patent
Imai (10) Patent No.: US 12,066,509 B2
(45) Date of Patent: Aug. 20, 2024

(54) MRI APPARATUS

(71) Applicant: CANON MEDICAL SYSTEMS CORPORATION, Otawara (JP)

(72) Inventor: Satoshi Imai, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 141 days.

(21) Appl. No.: 18/047,800

(22) Filed: Oct. 19, 2022

(65) Prior Publication Data

US 2023/0131526 A1 Apr. 27, 2023

(30) Foreign Application Priority Data

Oct. 22, 2021 (JP) ................. 2021-173032

(51) Int. Cl.
*G01R 33/36* (2006.01)
*A61B 5/00* (2006.01)
*A61B 5/055* (2006.01)
*G01R 33/48* (2006.01)

(52) U.S. Cl.
CPC .............. *G01R 33/36* (2013.01); *A61B 5/055* (2013.01); *A61B 5/6814* (2013.01); *A61B 5/6823* (2013.01); *G01R 33/48* (2013.01); *A61B 2560/0214* (2013.01)

(58) Field of Classification Search
CPC .... G01R 33/36; G01R 33/48; G01R 33/3685; A61B 5/055; A61B 5/6814; A61B 5/6823; A61B 2560/0214
See application file for complete search history.

(56) References Cited

U.S. PATENT DOCUMENTS

| | | | |
|---|---|---|---|
| 4,763,076 A | 8/1988 | Arakawa et al. | |
| 4,782,298 A | 11/1988 | Arakawa et al. | |
| 2010/0039113 A1* | 2/2010 | Vartiovaara | G01R 33/3657 324/322 |
| 2014/0132266 A1* | 5/2014 | Soejima | G01R 33/543 324/322 |
| 2019/0250225 A1* | 8/2019 | Tanji | G01R 33/36 |

FOREIGN PATENT DOCUMENTS

JP 01-164357 A 6/1989

* cited by examiner

*Primary Examiner* — Rodney A Bonnette
(74) *Attorney, Agent, or Firm* — Oblon, McClelland, Maier & Neustadt, L.L.P.

(57) ABSTRACT

In one embodiment, an MRI apparatus includes: a transmission circuit configured to apply a transmission pulse to an object; at least one radio frequency (RF) coil configured to include an active trap circuit provided with a PIN diode, and to receive a magnetic resonance signal from the object; a power supply circuit configured to apply a reverse bias voltage and a forward bias voltage to the PIN diode, and to apply multiple values of a forward current when the forward bias voltage is applied to the PIN diode; and a control circuit configured to control the power supply circuit in such a manner that the power supply circuit sets the forward current to the multiple values, depending on imaging conditions.

10 Claims, 9 Drawing Sheets

MRI APPARATUS

CROSS-REFERENCE TO RELATED APPLICATION

This application is based upon and claims the benefit of priority from Japanese Patent Application No. 2021-173032, filed on Oct. 22, 2021, the entire contents of which are incorporated herein by reference.

FIELD

Disclosed embodiments relate to a magnetic resonance imaging (MRI) apparatus.

BACKGROUND

An MRI apparatus is an imaging apparatus which magnetically excites nuclear spin of an object placed in a static magnetic field with a transmission pulse of a radio frequency (RF) signal having the Larmor frequency and reconstructs an image on the basis of magnetic resonance (MR) signals emitted from the object due to the excitation.

In an MRI apparatus, for example, a transmission pulse is applied to an object by a cylindrical coil called a whole body (WB) coil. In response to this application, an RF coil (also called a local coil) receives the MR signal emitted from the object.

The RF coil has one or more looped coil elements. Each coil element is provided with an active trap circuit that includes a PIN diode. Each active trap circuit is provided for achieving decoupling between plural coil elements, or for protecting electronic components connected to the coil elements from strong transmission pulses. In order to decouple the coil elements or protect the coil elements, it is necessary to apply an electric current in the forward direction of the PIN diode.

Recently, an RF coil called an array coil, in which a large number of coil elements are arranged in an array, has been in widespread use. Each of the large number of coil elements contained inside the array coil includes a PIN diode. Thus, entire power consumed by the PIN diodes can no longer be negligible.

BRIEF DESCRIPTION OF THE DRAWINGS

In the accompanying drawings:

FIG. 4A to FIG. 4E are schematic diagrams illustrating the relationship between bias control of PIN diodes and equivalent states of coil elements;

DETAILED DESCRIPTION

Hereinbelow, embodiments of the present invention will be described by referring to the accompanying drawings.

In one embodiment, an MRI apparatus includes: a transmission circuit configured to apply a transmission pulse to an object; at least one radio frequency (RF) coil configured to include an active trap circuit provided with a PIN diode, and to receive a magnetic resonance signal from the object; a power supply circuit configured to apply a reverse bias voltage and a forward bias voltage to the PIN diode, and to apply multiple values of a forward current when the forward bias voltage is applied to the PIN diode; and a control circuit configured to control the power supply circuit in such a manner that the power supply circuit sets the forward current to the multiple values, depending on imaging conditions.

Figure 1:
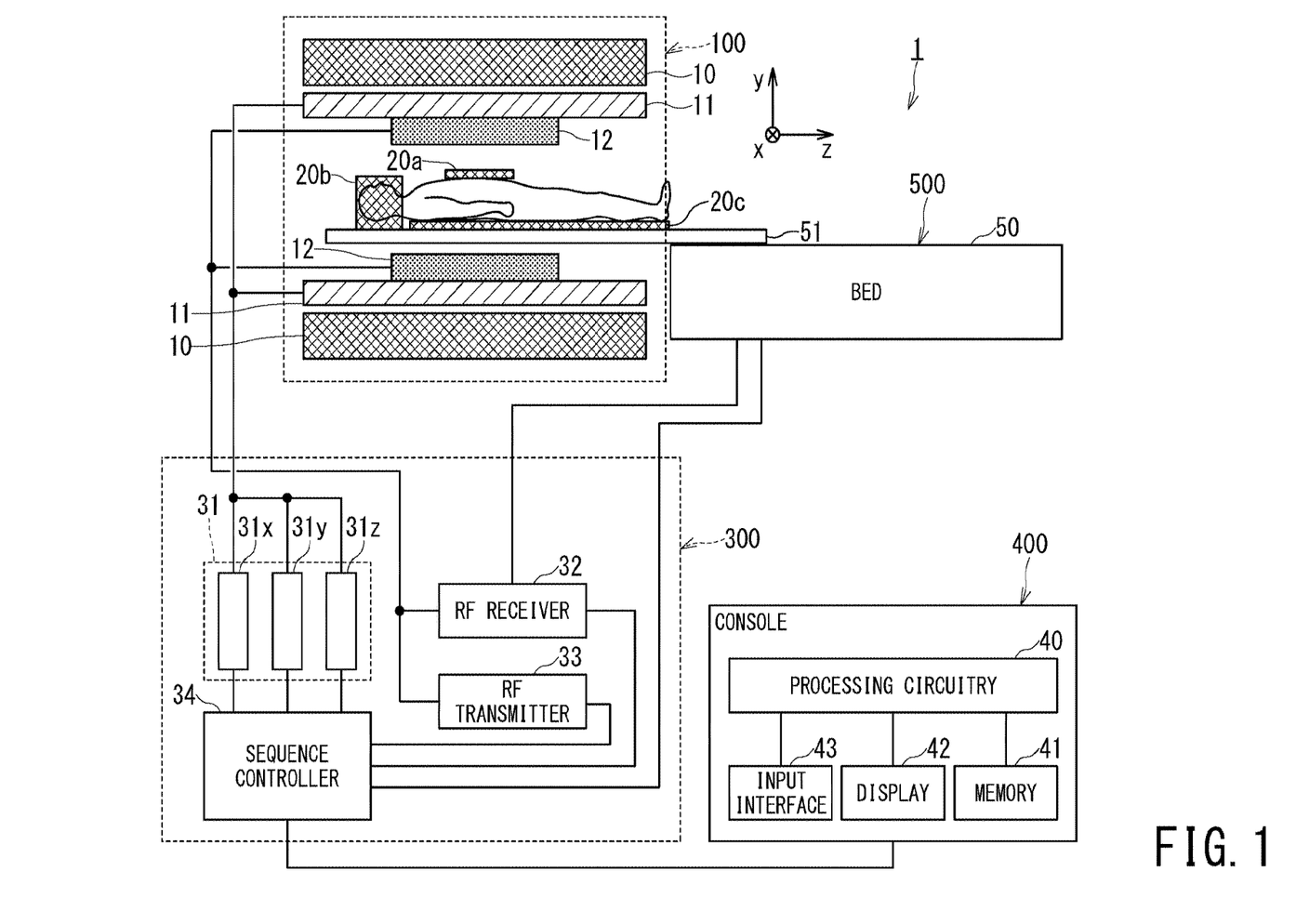
FIG. 1 is a configuration diagram illustrating an overall configuration of an MRI apparatus according to the present embodiment.

FIG. 1 is a block diagram illustrating an overall configuration of an MRI apparatus 1 according to the present embodiment. The MRI apparatus 1 according to the present embodiment includes a gantry 100, a bed 500, a control cabinet 300, and a console 400.

The gantry 100 includes a static magnetic field magnet 10, a gradient coil 11, and a whole body (WB) coil 12, and these components are housed in a cylindrical housing. The bed 500 includes a bed body 50 and a table 51. The MRI apparatus 1 includes at least one radio frequency coil 20 (hereinafter, referred to as the RF coil 20) disposed close to an object.

The control cabinet 300 includes: a static magnetic field power supply (not shown); three gradient coil power supplies 31 (31x for an X-axis, 31y for a Y-axis, and 31z for a Z-axis); an RF receiver 32; an RF transmitter 33; and a sequence controller 34.

The static magnetic field magnet 10 of the gantry 100 is substantially in the form of a cylinder and generates a static magnetic field inside a bore, which is a space inside the cylindrical structure of the static magnetic field magnet 10 and is also an imaging space of an object such as a patient. The static magnetic field magnet 10 includes a superconducting coil inside, and the superconducting coil is cooled down to an extremely low temperature by liquid helium. The static magnetic field magnet 10 generates a static magnetic field by supplying the superconducting coil with an electric current provided from the static magnetic field power supply (not shown) in an excitation mode. Afterward, the static magnetic field magnet 10 shifts to a persistent current mode, and the static magnetic field power supply is separated. Once it enters the persistent current mode, the static magnetic field magnet 10 continues to generate a strong static magnetic field for a long time, for example, over one year. Note that the static magnetic field magnet 10 may be configured as a permanent magnet.

The gradient coil 11 is also substantially in the form of a cylinder and is fixed to the inside of the static magnetic field magnet 10. This gradient coil 11 applies gradient magnetic fields to the object in the respective directions of the X-axis, the Y-axis, and the Z-axis by using electric currents supplied from the gradient coil power supplies 31x, 31y, and 31z.

The bed body 50 of the bed 500 can move the table 51 in the vertical direction and moves the table 51 with the object placed thereon to a predetermined height before imaging. Afterward, during the imaging, the bed body 50 moves the table 51 in the horizontal direction so as to move the object to the inside of the bore.

The WB coil 12 is shaped substantially in the form of a cylinder so as to surround the object and is fixed to the inside of the gradient coil 11. The WB coil 12 applies RF pulses transmitted from the RF transmitter 33 to the object, and receives MR signals emitted from the object due to excitation of hydrogen nuclei.

The RF coil 20 receives MR signals emitted from the object at a position close to the body surface of the object. As described below, the RF coil 20 includes one or a plurality of coil elements. There are various types for the RF coil 20 depending on a body part of the object to be imaged. For example, as the RF coils 20, FIG. 1 illustrates a body coil 20a for imaging the chest and/or abdomen of the object, a head coil 20b for imaging the head, and a spine coil 20c for imaging the spine.

The RF transmitter 33 transmits RF pulses to the WB coil 12 based on the instruction from the sequence controller 34. The RF receiver 32 detects MR signals received by the WB coil 12 and/or the RF coil 20, digitizes the detected MR signals, and transmits the digitized MR signals to the sequence controller 34.

The sequence controller 34 performs a scan of the object by driving the gradient coil power supplies 31, the RF transmitter 33, and the RF receiver 32 under the control of the console 400. The sequence controller 34 receives MR signals acquired by the scan from the RF receiver 32, and transmits the received MR signals to the console 400.

The sequence controller 34 includes processing circuitry (not shown). This processing circuitry is configured as a processor for executing predetermined programs or is configured as hardware such as a field programmable gate array (FPGA) and an application specific integrated circuit (ASIC), for example.

The console 400 is configured as a computer that includes processing circuitry 40, a memory 41, an input interface 43; and a display 42.

The memory 41 is a recording medium including a read-only memory (ROM) and/or a random access memory (RAM) in addition to an external memory device such as a hard disk drive (HDD) and an optical disc device. The memory 41 stores various programs to be executed by the processor of the processing circuitry 40 as well as various data and information.

The input interface 43 includes various devices for an operator to input various data and information, and is configured of a mouse, a keyboard, a trackball, and/or a touch panel, for example. The input interface 43 also includes an interface circuit between these devices and the processing circuitry 40.

The display 42 is a display device such as a liquid crystal display panel, a plasma display panel, and an organic EL panel.

The processing circuitry 40 is a circuit provided with a central processing unit (CPU) and/or a special-purpose or general-purpose processor, for example. The processor implements various functions described below by executing the programs stored in the memory 41. The processing circuitry 40 may be configured of hardware such as an FPGA and an ASIC. The various functions described below can also be implemented by such hardware. Additionally, the processing circuitry 40 can implement the various functions by combining hardware processing and software processing based on its processor and programs.

The console 400 comprehensively controls the MRI apparatus 1. Specifically, the console 400 receives various information items and instructions including imaging conditions through the input interface 43 such as a mouse and/or a keyboard that are operated by an operator such as a medical imaging technologist. The processing circuitry 40 causes the sequence controller 34 to perform a scan on the basis of the inputted imaging conditions, and reconstructs an image on the basis of raw data transmitted from the sequence controller 34. The reconstructed image is displayed on the display 42 or stored in the memory 41.

Figure 2:
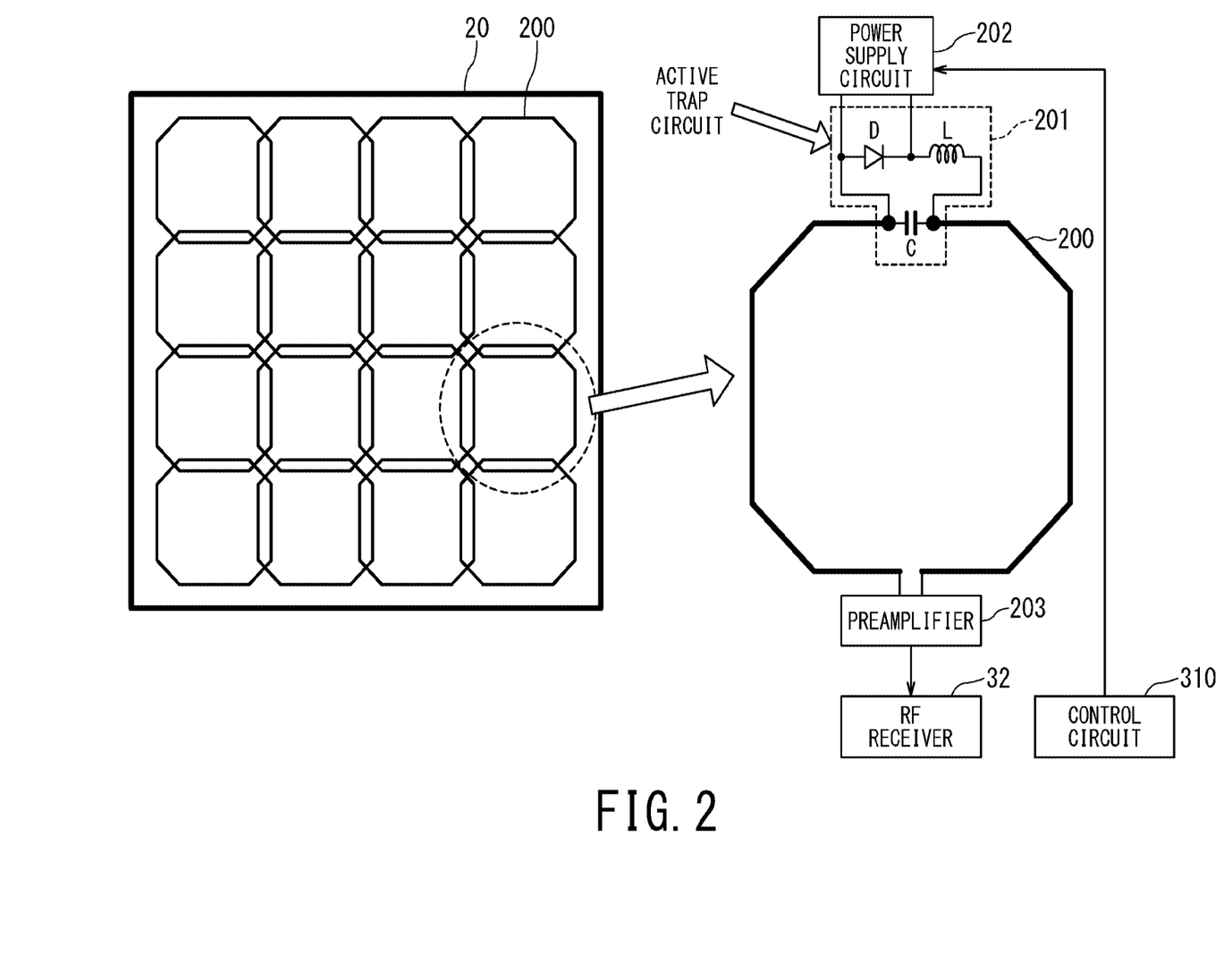
FIG. 2 is a schematic diagram illustrating a configuration of an RF coil and coil elements included in the RF coil.

The left part of FIG. 2 illustrates a configuration of the RF coil 20 (for example, the body coil 20a). As shown in the left part of FIG. 2, the RF coil 20 has a large number of coil elements 200, and the large number of coil elements 200 are arranged in an array. In the case of the left part of FIG. 2, sixteen coil elements 200 are arranged in four rows and four columns.

The right part of FIG. 2 illustrates a configuration of one coil element 200 extracted from the RF coil 20, including some electronic circuits connected to this extracted coil element 200. The coil element 200 is formed of a loop-shaped conductor. In a part of the path of this loop-shaped conductor, a capacitor C, which is configured as one of the components of the active trap circuit 201, is inserted in series.

The active trap circuit 201 is composed of the above-described capacitor C, a PIN diode D, and an inductor L. A series circuit composed of the PIN diode D and the inductor L is connected to the capacitor C in parallel.

A power supply circuit 202 is connected to the anode and cathode of the PIN diode. The power supply circuit 202 is configured to switchably apply a forward bias voltage and a reverse bias voltage to the PIN diode D. In particular, the power supply circuit 202 of the MRI apparatus 1 according to the present embodiment is configured in such a manner that multiple values of a forward current can be set when the forward bias voltage is applied to the PIN diode D.

A control circuit 310 is connected to the power supply circuit 202. Based on a control signal and/or an instruction command transmitted from the control circuit 310, the power supply circuit 202 performs switching between the forward bias voltage and the reverse bias voltage, and switching between the multiple forward current values when the forward bias voltage is applied.

The coil element 200 is connected to a preamplifier 203 in addition to the active trap circuit 201. The preamplifier 203 amplifies the MR signal received by the coil element 200 with low noise, and transmits the amplified MR signal to the subsequent RF receiver 32.

Figure 3:
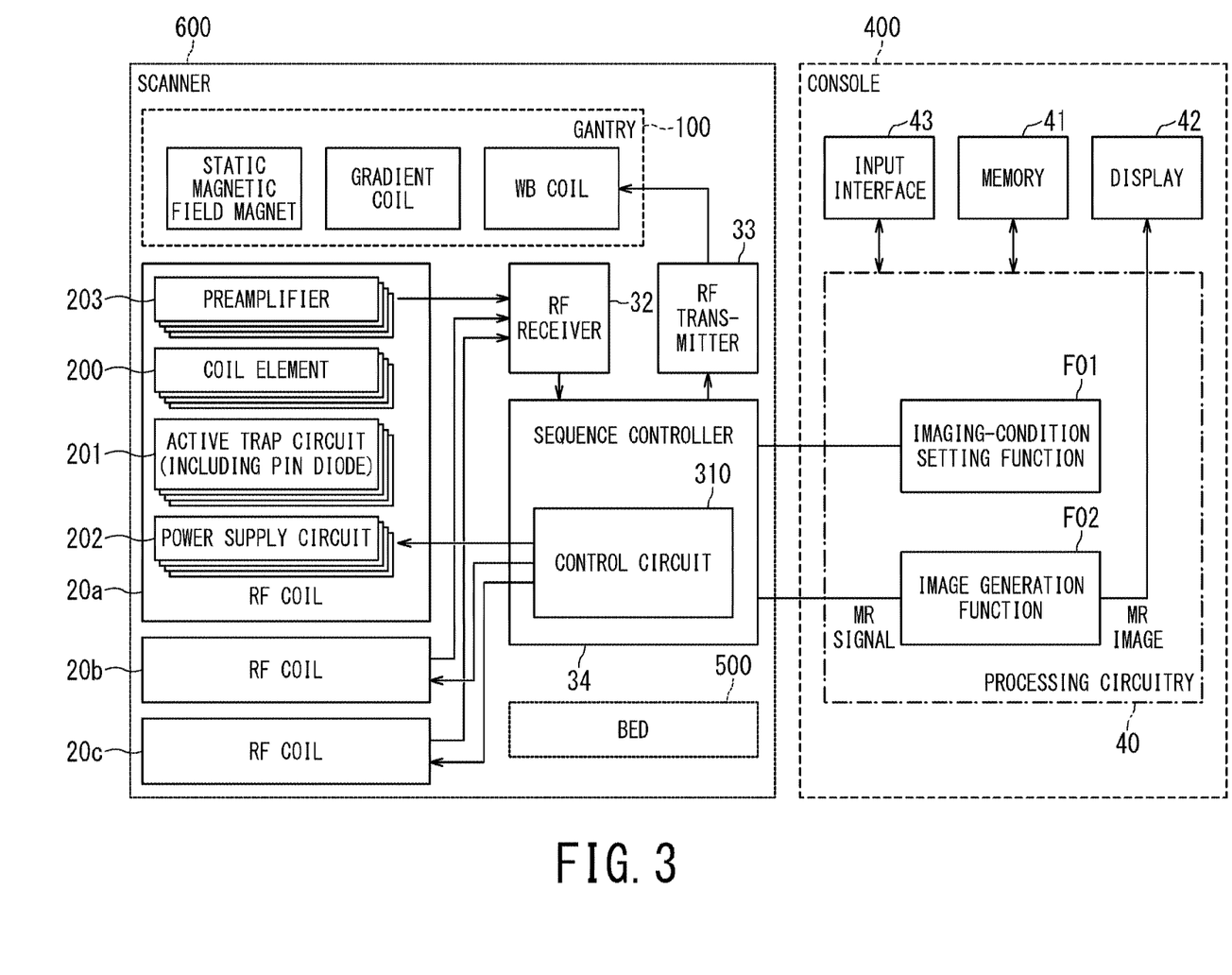
FIG. 3 is a functional block diagram of the MRI apparatus according to the present embodiment.

FIG. 3 is a functional block diagram of the MRI apparatus 1 of the present embodiment, particularly focusing on the functions related to the control of the active trap circuit 201 in the RF coil 20. The left side of FIG. 3 is a block corresponding to a scanner 600, and the right side of FIG. 3 is a block corresponding to the console 400. Note that, of the configuration of the MRI apparatus 1 shown in FIG. 1, all the components excluding the console 400 (i.e., the gantry 100 including the static magnetic field magnet 10, the control cabinet 300 including the sequence controller 34, and the bed 500) are called the scanner 600.

In an example shown in FIG. 3, the scanner 600 includes three RF coils 20 (i.e., the RF coil 20a, the RF coil 20b, and the RF coil 20c). the RF coil 20a may be, for example, a body coil 20a, although the number and type of the RF coils 20 provided in the scanner 600 are not limited to specific number and specific type.

Each of the RF coils 20a, 20b, and 20c has a plurality of coil elements 200. A set of one active trap circuit 201, one power supply circuit 202, and one preamplifier 203 is provided for each of the coil elements 200 individually.

The MR signals received by the plurality of coil elements 200 of the RF coils 20a, 20b, and 20c are amplified by the corresponding preamplifiers 203 and inputted to the RF receiver 32. The RF receiver 32 digitizes the MR signals and transmits the digitized MR signals to the sequence controller 34. The sequence controller 34 transmits the received MR signals to the console 400.

The console 400 includes the processing circuitry 40 as described above, and the processor included in the processing circuitry 40 executes various programs to realize various functions. The processing circuitry 40 implements an imaging-condition setting function F01 and an image generation function F02 as shown in FIG. 3, for example.

The image generation function F02 performs reconstruction processing on the digitized MR signals (i.e., k-space data) transmitted from the sequence controller 34 by using, for example, Fourier transform so as to generate an MR image. The generated MR image is displayed on the display 42, for example.

The imaging-condition setting function F01 sets various imaging conditions, which are inputted or selected by a user via the input interface 43, on the sequence controller 34. For example, the imaging conditions include: information on a body part to be imaged and/or an imaging region; information on resolution such as number of slices and matrix size; information on imaging methods (i.e., type of pulse sequence) such as FSE (fast spin echo), SSFP (steady-state free precision), and DWI (diffusion weighted imaging); and values of various parameters in the pulse sequence. The various parameters include: a flip angle or transmission peak power of the RF pulse (i.e., transmission pulse) such as an excitation pulse and a refocus pulse; a repetition period of the RF pulse; and parameter values related to strength and application timing of the gradient pulse, for example.

The sequence controller 34 further determines more detailed imaging conditions and their parameters based on the imaging conditions, which have been set by the imaging-condition setting function F01 of the console 400.

For example, depending on the determined body part to be imaged, such as the head, chest, abdomen, and spine, the RF coil 20 to be used for imaging is selected (i.e., determined) from the RF coils 20 attached to the object including the head coil 20b, the body coil 20a, and the spine coil 20c. Alternatively, the user may select the type of the RF coil 20 to be used for imaging, as one of the imaging conditions.

Further, the sequence controller 34 may determine the position and range of the FOV (field of view) according to information on the imaging region that is set as an imaging condition. Based on the determined position and range of the FOV, the sequence controller 34 may distinguish between the coil elements 200 corresponding to the region inside the FOV and the coil elements 200 corresponding to the region outside the FOV, among all the coil elements 200 included in the selected RF coil 20.

Further, the sequence controller 34 determines: parameters related to RF pulses in the pulse sequence used for imaging (for example, waveform, generation timing, transmission peak power of each RF pulse); and parameters related to gradient pulses (for example, waveform, generation timing, strength of the gradient pulse in each of the X-axis, Y-axis, and Z-axis directions), based on: information on the position and range of the determined FOV; information on the resolution and matrix size; information on the type of pulse sequence; and information on the flip angle of each RF pulse.

In response to a command to start imaging, the sequence controller 34 causes the RF transmitter 33 to generate RF pulses in accordance with the determined parameters related to the RF pulses, and causes the gradient magnetic field power supplies 31x, 31y, 31z to generate gradient pulses in accordance with the determined parameters related to the gradient pulses.

As described above, each active trap circuit 201 in the RF coil 20 of the present embodiment is provided with the power supply circuit 202 for driving the PIN diode D, and the control circuit 310 is connected to each power supply circuit 202 as shown in FIG. 3.

The control circuit 310 may be provided, for example, inside the sequence controller 34. The control circuit 310 controls the power supply circuit 202, depending on the imaging conditions determined by the sequence controller 34, to switch the forward bias voltage and the reverse bias voltage to be applied to the PIN diode D in the active trap circuit 201. The control circuit 310 also controls the power supply circuit 202 to apply forward currents having different electric-current values to the PIN diode D depending on the imaging conditions when the forward bias voltage is applied.

The control circuit 310 does not necessarily have to be provided in the sequence controller 34 and may be provided in the console 400. Alternatively, one control circuit 310 may be individually provided for each of the RF coils 20.

FIG. 4A to FIG. 4E are schematic diagrams illustrating the control of the forward bias voltage and the reverse bias voltage for the PIN diode D described above, and the relationship between the control of the forward current value and the equivalent state of the coil elements 200.

In the example as shown in FIGS. 4A to 4E, the control circuit 310 switches between a first state in which the power supply circuit 202 applies the reverse bias voltage to the PIN diode D and a second state in which the power supply circuit 202 applies the forward bias voltage. In the second state of applying the forward bias voltage, the control circuit 310 switches the forward current in multiple stages, for example, three stages of "large", "medium", and "small".

Figure 4A:
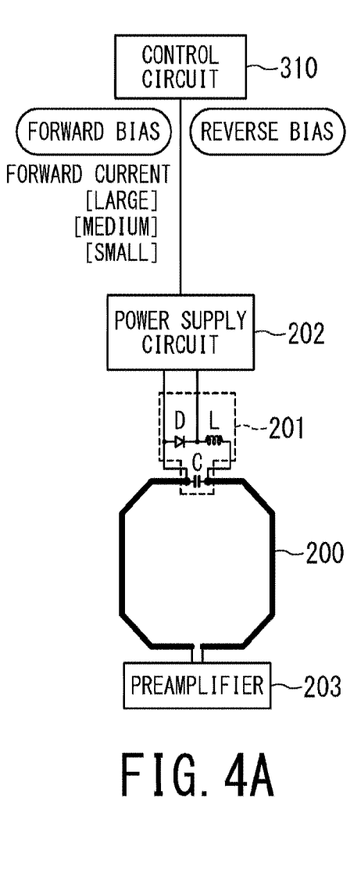
Figure 4B:
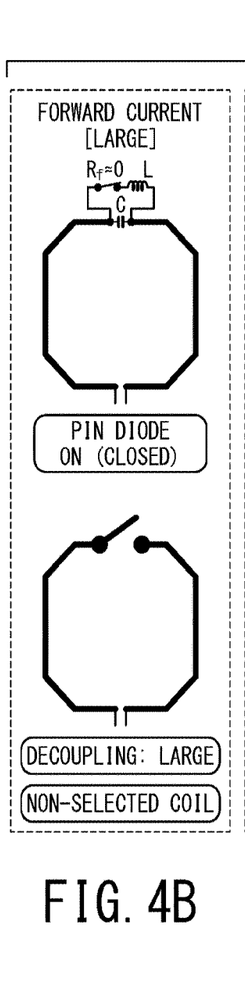

FIG. 4B illustrates a state in which the forward bias voltage is applied to the PIN diode D and a "large" forward current equal to or greater than a predetermined value flows through the PIN diode D (i.e., a state in which the forward current value is large). In this state shown in the upper part of FIG. 4B, the PIN diode D is ON (i.e., closed), and the equivalent resistance value $R_f$ of the PIN diode D with respect to a radio frequency (e.g., a Larmor frequency) signal becomes almost zero. As a result, the active trap circuit 201 forms a parallel-resonant circuit composed of the capacitor C and the inductor L.

The capacitance of the capacitor C and the inductance of the inductor L are selected such that the resonant frequency of this parallel-resonant circuit matches the Larmor frequency. Thus, in the state in which the forward current value of the PIN diode D is large, the impedance Z of the parallel-resonant circuit becomes infinite with respect to the MR signal having the Larmor frequency, the coil element 200 becomes open at the position of the parallel-resonant circuit as shown in the lower part of FIG. 4B, and the MR signal does not flow through the coil element 200.

Hence, in the state in which the forward current value of the PIN diode D is large, there is no induction from other coil elements 200, i.e., the degree of decoupling is maximized. In this state, no MR signal flows through the coil element 200, and thus, the coil element 200 functions as a non-selected coil element 200 that does not take part in generating an MR image.

In the state in which the forward current value of the PIN diode D is large, the power consumption of the PIN diode D is the largest.

Figure 4C:
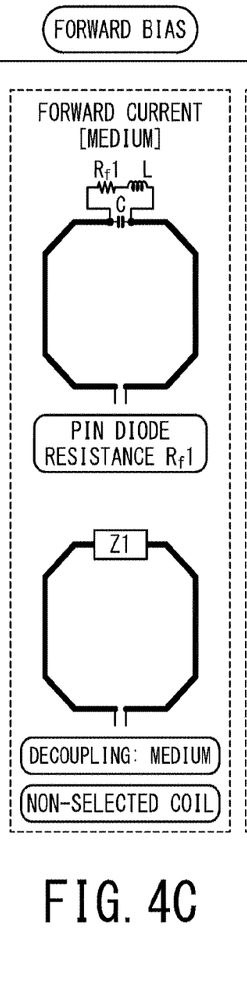

FIG. 4C illustrates a state in which the forward bias voltage is applied to the PIN diode D and the forward current value of the PIN diode D is "medium" (i.e., smaller than the predetermined value of the state of having the "large" forward current value shown in FIG. 4B). In this state shown in the upper part of FIG. 4C, the resistance value $R_f$ of the PIN diode D is not zero but shows a predetermined resistance value $R_f1$ with respect to the radio frequency signal. As a result, the capacitor C of the active trap circuit 201 is connected to the series circuit of the resistance value $R_f1$ and the inductor L in parallel. In this state shown in the lower part of FIG. 4C, even at the Larmor frequency, the impedance Z1 of the active trap circuit 201 does not become infinite but exhibits a finite value Z1.

In this state in which the forward current value of the PIN diode D is medium, the MR signal flows to some extent, but the current value of the MR signal is considerably limited, so the coil element 200 functions as a non-selected coil element 200 that does not take part in generating an MR image.

In this state, while this coil element is induced by other coil elements 200 to some extent (i.e., the degree of decoupling is medium), decoupling can be achieved under the condition where this coil element 200 is sufficiently separated from the other coil elements 200 (e.g., is not close to, or adjacent to any other coil element 200).

In the state in which the forward current value of the PIN diode D is medium, the power consumption of the PIN diode D is smaller than in the state of having the "large" forward current value.

Figure 4D:
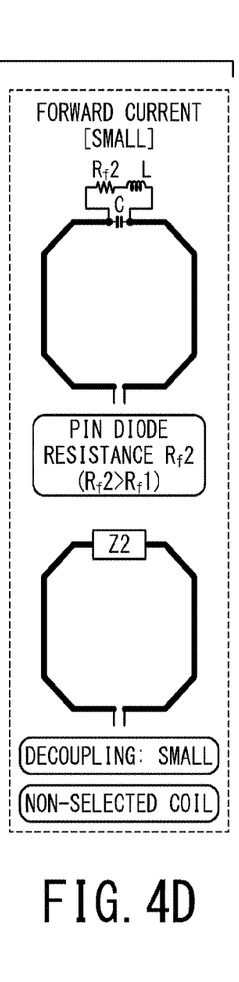

FIG. 4D illustrates a state in which the forward bias voltage is applied to the PIN diode D and the forward current value is set to be even smaller than the state of having the "medium" forward current value (i.e., a state where the forward current value is "small"). In this state shown in the upper part of FIG. 4D, the resistance value $R_f$ of the PIN diode D is not zero either but shows a predetermined resistance value $R_f2$ with respect to the radio frequency signal. However, the resistance value $R_f2$ is larger than the resistance value $R_f1$ in the state of having the "medium" forward current value ($R_f2 > R_f1$).

Also in this state, the capacitor C of the active trap circuit 201 is connected to the series circuit of the resistance value $R_f2$ and the inductor L in parallel. In this state shown in the lower part of FIG. 4D, even at the Larmor frequency, the impedance Z2 of the active trap circuit 201 does not become infinite but shows a finite value Z2. However, the impedance Z2 in the state of having the "small" forward current value shows a smaller value than the impedance Z1 in the state of having the "medium" forward current value.

Also, in this state in which the forward current value of the PIN diode D is small, the MR signal flows to some extent, but the current value of the MR signal is considerably limited, so this coil element 200 functions as a non-selected coil element 200 that does not take part in generating an MR image.

As compared with the state in which the forward current value of the PIN diode D is medium, the degree of induction from other coil elements 200 becomes larger and the degree of decoupling becomes smaller in the state of having the "small" forward current value. That is, the induced current caused by other coil elements 200 becomes larger. However, in this state of having the "small" forward current value, decoupling can also be achieved under the condition where other coil elements 200 are separated from this coil elements 200 by a certain distance or more.

In the state in which the forward current value of the PIN diode D is small, the power consumption of the PIN diode D is smaller than in the state of having the "medium" forward current value.

Figure 4E:
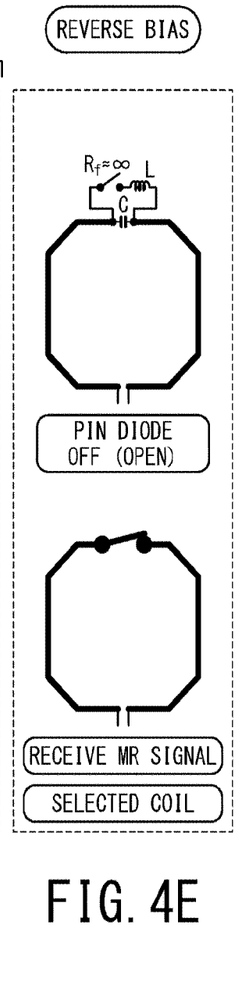

FIG. 4E illustrates a state in which the reverse bias voltage is applied to the PIN diode D. In this state shown in the upper part of FIG. 4E, the PIN diode D is OFF (i.e., open) and the equivalent resistance value $R_f$ of the PIN diode D with respect to the radio frequency signal becomes almost infinite. As a result, the active trap circuit 201 connected to the coil elements 200 in series is substantially composed of the capacitor C alone.

In this state, the impedance of the capacitor C at the Larmor frequency becomes almost zero, and the coil element 200 is almost equivalent to the state in which a switch at the position of the active trap circuit 201 is turned on as shown in the lower part of FIG. 4E.

In other words, application of the reverse bias voltage to the PIN diode D enables the coil elements 200 to satisfactorily receive the MR signal, and the coil element 200 functions as a selected coil element 200 that is used for generating an MR image.

The state of applying the reverse bias voltage to the PIN diode D is the state in which the power consumption of the PIN diode D is the smallest or minimized. However, this is also a state in which electronic components such as the preamplifier 203 and the PIN diode D of the active trap circuit 201 are most likely to be damaged when a high power such as an RF pulse is applied.

In the MRI apparatus 1 of the present embodiment, the above-described bias control for the PIN diode D of the active trap circuit 201 is performed in multiple stages depending on imaging conditions. This multistage or multistep bias control reduces the power consumption of the PIN diode D more than the conventional technology. Hereinbelow, a description will be given of several examples of the multistage bias control for the PIN diode D.

Figure 5:
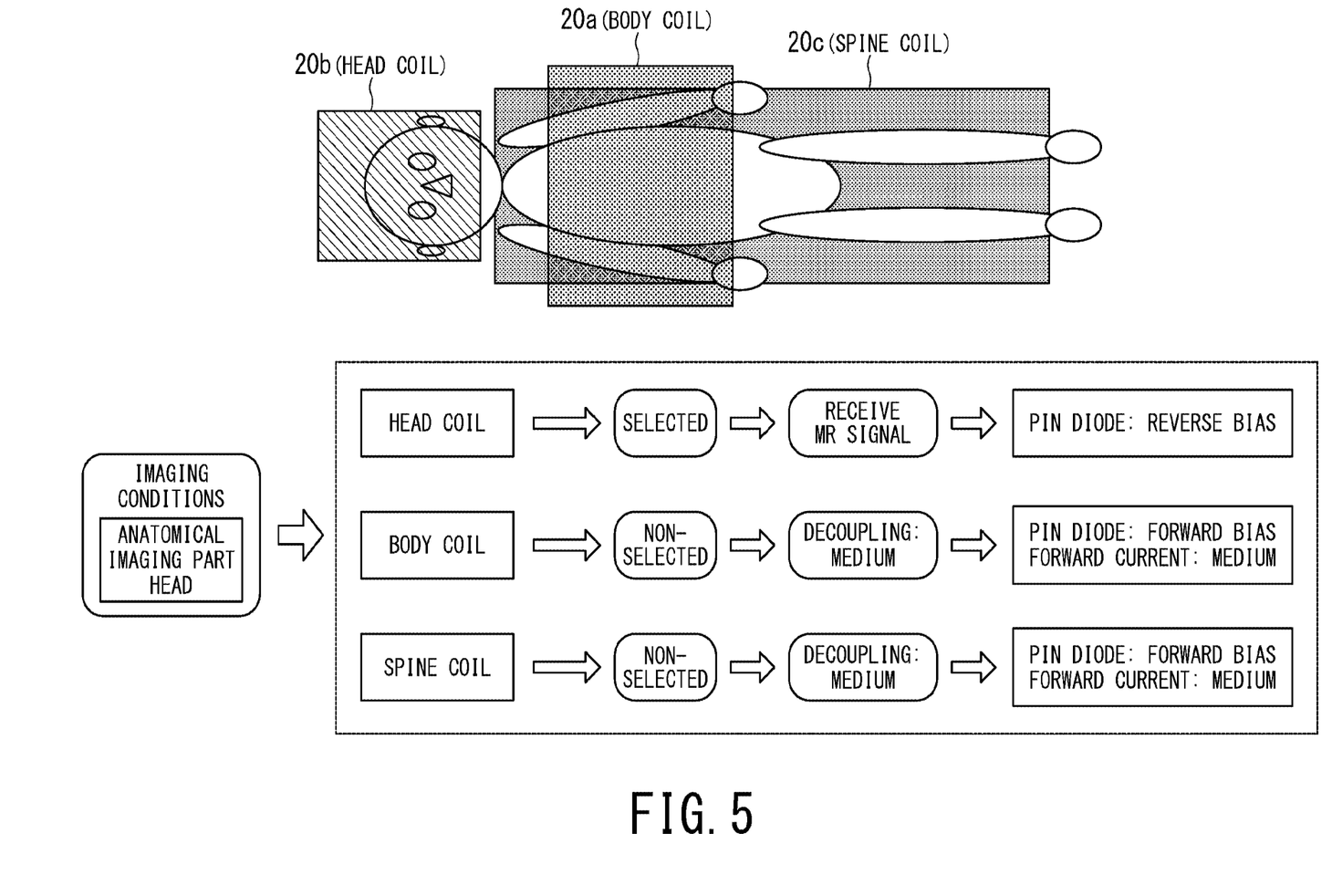
FIG. 5 is a schematic diagram illustrating a first example of multistage bias control for a PIN diode.

FIG. 5 is a schematic diagram illustrating a first example. In the first example, as shown in the upper part of FIG. 5, the head coil 20b, the body coil 20a, and the spine coil 20c are disposed around the object as one aspect of a plurality of RF coils 20.

For example, when the head is set to be the body part to be imaged as an imaging condition, the sequence controller 34 or the control circuit 310 selects the head coil 20b as the RF coil 20 to be used for imaging, and the other two coils 20 (i.e., body coil 20a and spine coil 20c) are treated as non-selected coils.

In this case, the head coil 20b is an RF coil corresponding to the imaging region and functions as a selected coil (i.e., first RF coil) for receiving MR signals, so the control circuit 310 causes each power supply circuit 202 to apply the reverse bias voltage to the PIN diode D of each coil element 200 in the head coil 20b.

The body coil 20a and the spine coil 20c do not correspond to the body part to be imaged, and thus, function as non-selected coils (i.e., second RF coils) that are not used for imaging.

In the conventional technology, in order to reliably achieve decoupling from the selected coil(s), the forward bias current of a predetermined current value or more is applied to each non-selected coil for maximizing the degree of decoupling. That is, both the body coil 20a and the spine coil 20c are set to the state of having the "large" forward current value shown in FIG. 4B, and in this state, the power consumption of the PIN diode D is the largest or maximized.

However, the non-selected coils (i.e., the body coil 20a and the spine coil 20c) and the selected coil (i.e., the head coil 20b) are not close enough to overlap each other, and thus, it is not necessarily required to maximize the degree of decoupling between the non-selected coils and the selected coil, and a medium degree of decoupling can be sufficient.

Accordingly, in the first example, the forward current value of the PIN diode D is set to a value smaller than a predetermined value in the state of having the largest decoupling such that the degree of decoupling of the non-selected body coil 20a and spine coil 20c becomes medium. That is, both the body coil 20a and the spine coil 20c are set to the state of having the "medium" forward current value shown in FIG. 4C. As a result, the power consumption of the PIN diode D can be reduced more than the conventional technology.

Figure 6:
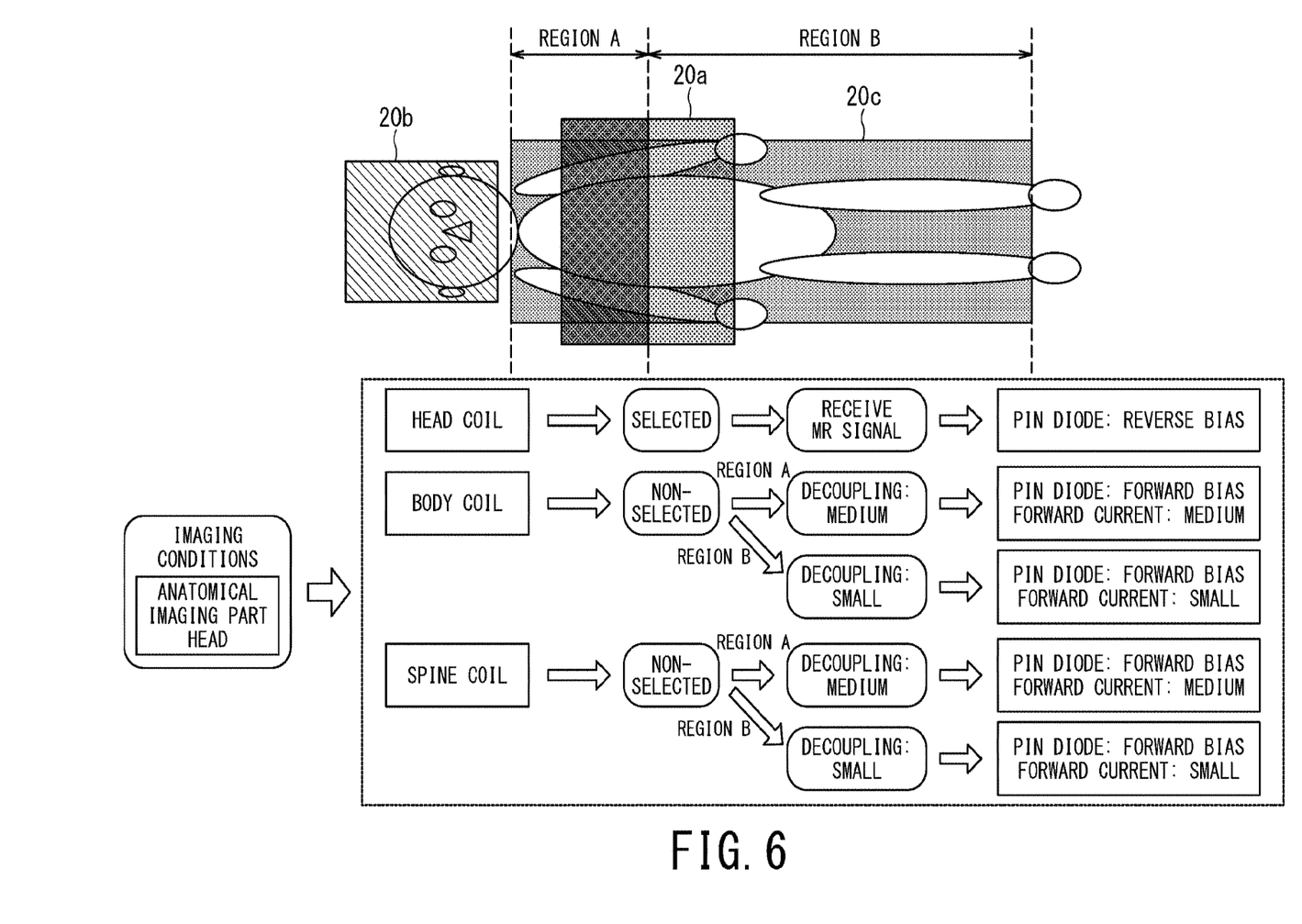
FIG. 6 is a schematic diagram illustrating a modification of the first example of the multistage bias control for a PIN diode.

FIG. 6 illustrates a modification of the first example. In the modification of the first example, the entire region of the non-selected coils is divided into a plurality of regions depending on the distance from the selected coil, and the forward current value of the PIN diode D of the coil elements 200 in each divided region is made smaller as the distance from the selected coil increases.

For instance, in the modification shown in FIG. 6, the entire region of the non-selected body coil 20a and the non-selected spine coil 20c is divided into a region A close to, or adjacent to the selected head coil 20b and a region B far from the selected head coil 20b. Since the region B is farther from the head coil 20b, the degree of decoupling from the head coil 20b can be made even smaller than the degree of decoupling of the region A.

Thus, in the modification of the first example, each PIN diode D in the region A of the body coil 20a and the spine coil 20c is set to the state of having the "medium" forward current value similarly to the first example, while each PIN diode D in the region B of the body coil 20a and the spine coil 20c is set to the state of having the "small" forward current value which is even smaller than that in the region A.

Such control of the forward current in the modification of the first example can further reduce the power consumption of the PIN diode D than the first example.

Figure 7:
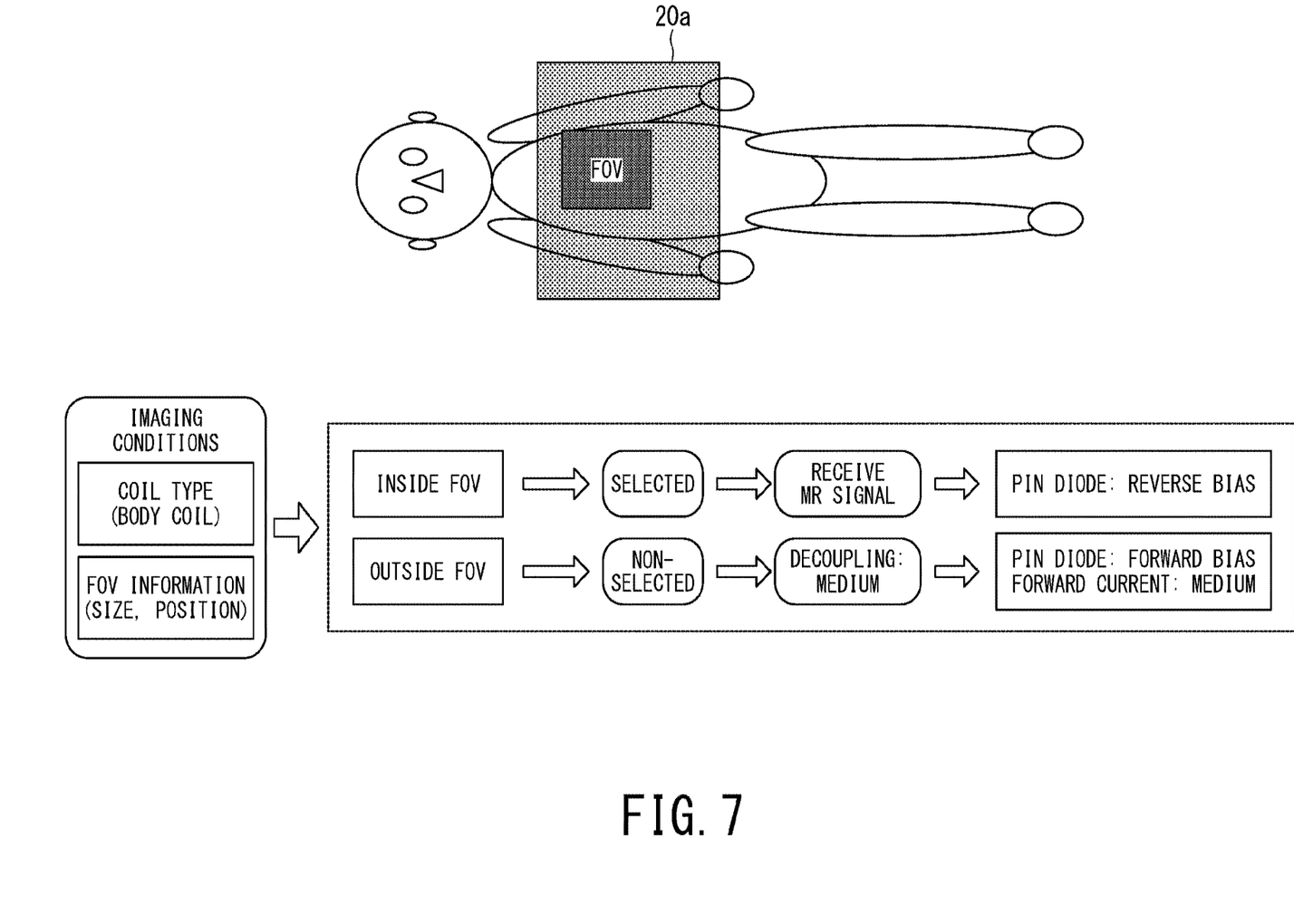
FIG. 7 is a schematic diagram illustrating a second example of the multistage bias control for a PIN diode.

FIG. 7 illustrates a second example. In the second example, as shown in the upper part of FIG. 7, the body coil 20a is disposed on the object as one aspect of at least one RF coil 20 used for imaging.

As an imaging condition, an imaging region, i.e., FOV (field of view) is set by the user. For example, as illustrated in FIG. 7, a region of a predetermined range including the heart of the object is set as the FOV.

When the FOV is set, among the plurality of coil elements 200 included in the body coil 20a, the sequence controller 34 or the control circuit 310 selects one or more coil elements 200 corresponding to the region of the FOV and does not select any of the coil elements 200 corresponding to the outside of the FOV.

The control circuit 310 controls each power supply circuit 202 in such a manner that the selected coil elements 200 corresponding to the region of the FOV is switched to the state capable of receiving MR signals and the reverse bias voltage is applied to the PIN diode D of the selected coil elements.

Note that the coil elements 200 inside the FOV and the coil elements 200 outside the FOV are not close enough to overlap each other, thus, it is not necessarily required to maximize the degree of decoupling and the medium degree of decoupling can be sufficient.

Thus, in the second example, the forward current value of the PIN diode D is set to a value smaller than the predetermined value in the state of having the largest decoupling, such that the degree of decoupling between the coil elements 200 inside the FOV and the coil elements 200 outside the FOV becomes medium. In other words, the coil elements 200 outside the FOV are set to the state of having the "medium" forward current value as shown in FIG. 4C.

In the conventional technology, the forward bias current of a predetermined value or more is applied to the PIN diode D of the coil elements 200 outside the FOV such that the degree of decoupling from the coil elements 200 inside the FOV is maximized. In other words, the PIN diode D of the coil element 200 outside the FOV is set to the state of having the "large" forward current value as shown in FIG. 4B.

In the second example, by setting the coil elements 200 outside the FOV to the state of having the "medium" forward current value shown in FIG. 4C, the power consumption of the PIN diode D is reduced more than the conventional technology.

Figure 8:
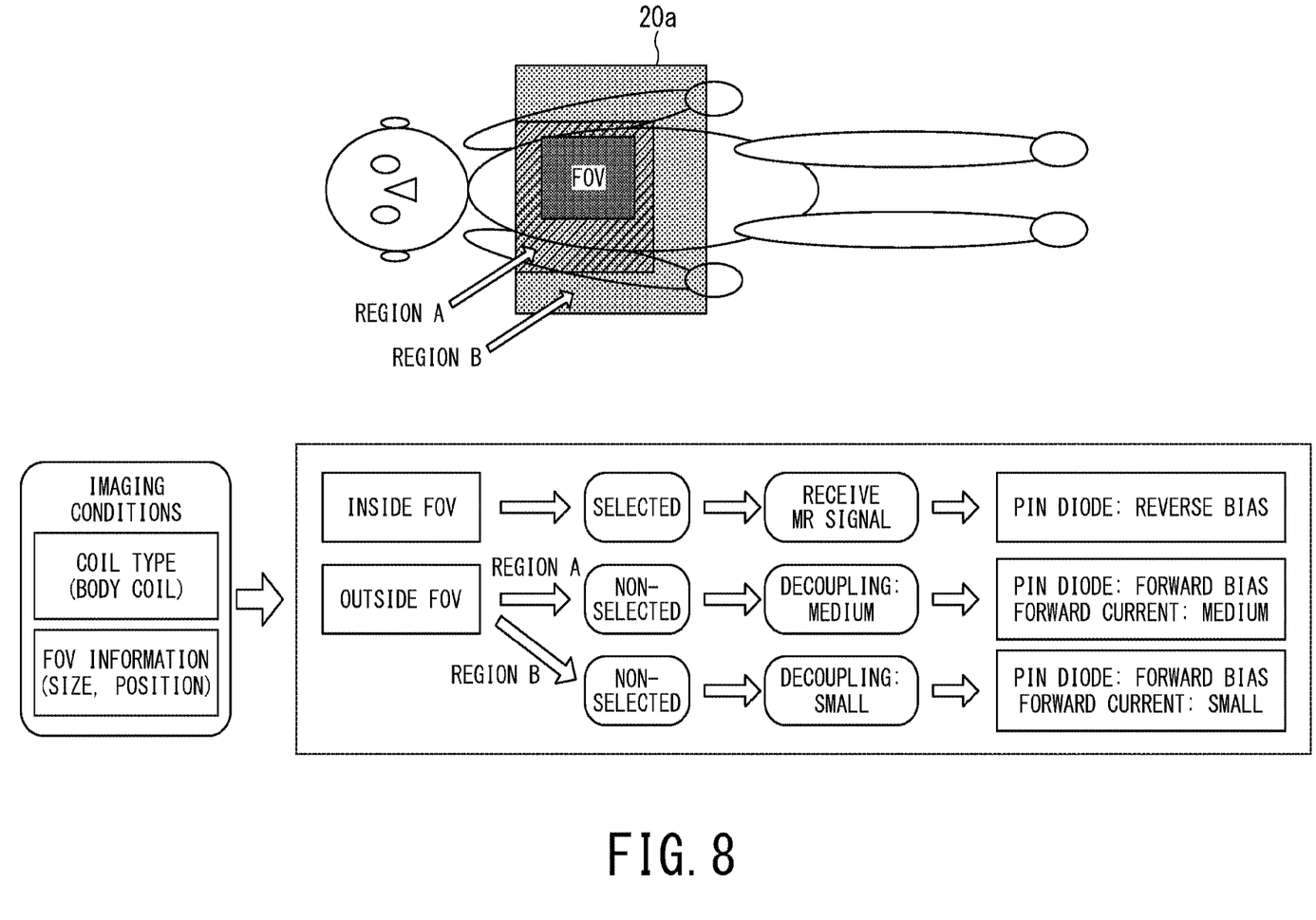
FIG. 8 is a schematic diagram illustrating a modification of the second example of the multistage bias control for a PIN diode.

FIG. 8 illustrates a modification of the second example. In the modification of the second example, the entire region of the body coil 20a is divided into a plurality of regions depending on the distance from the FOV, such that the forward current value of the PIN diode D in the region farther from the FOV (i.e., region B in the example of FIG. 8) becomes smaller than that in the region closer to the FOV (i.e., region A in the example of FIG. 8).

For instance, in the modification shown in FIG. 8, the forward current value of the PIN diode D in the region A is the same as that in the second example, and the forward current value of the PIN diode D in the region B is set to a value smaller than the forward current value in the region A. That is, the forward current value of the PIN diode D in the region B is set to the state of having the "small" forward current value as shown in FIG. 4D.

Such control of the forward current in the modification of the second example reduces the power consumption of the PIN diode D more than the second example.

Figure 9:
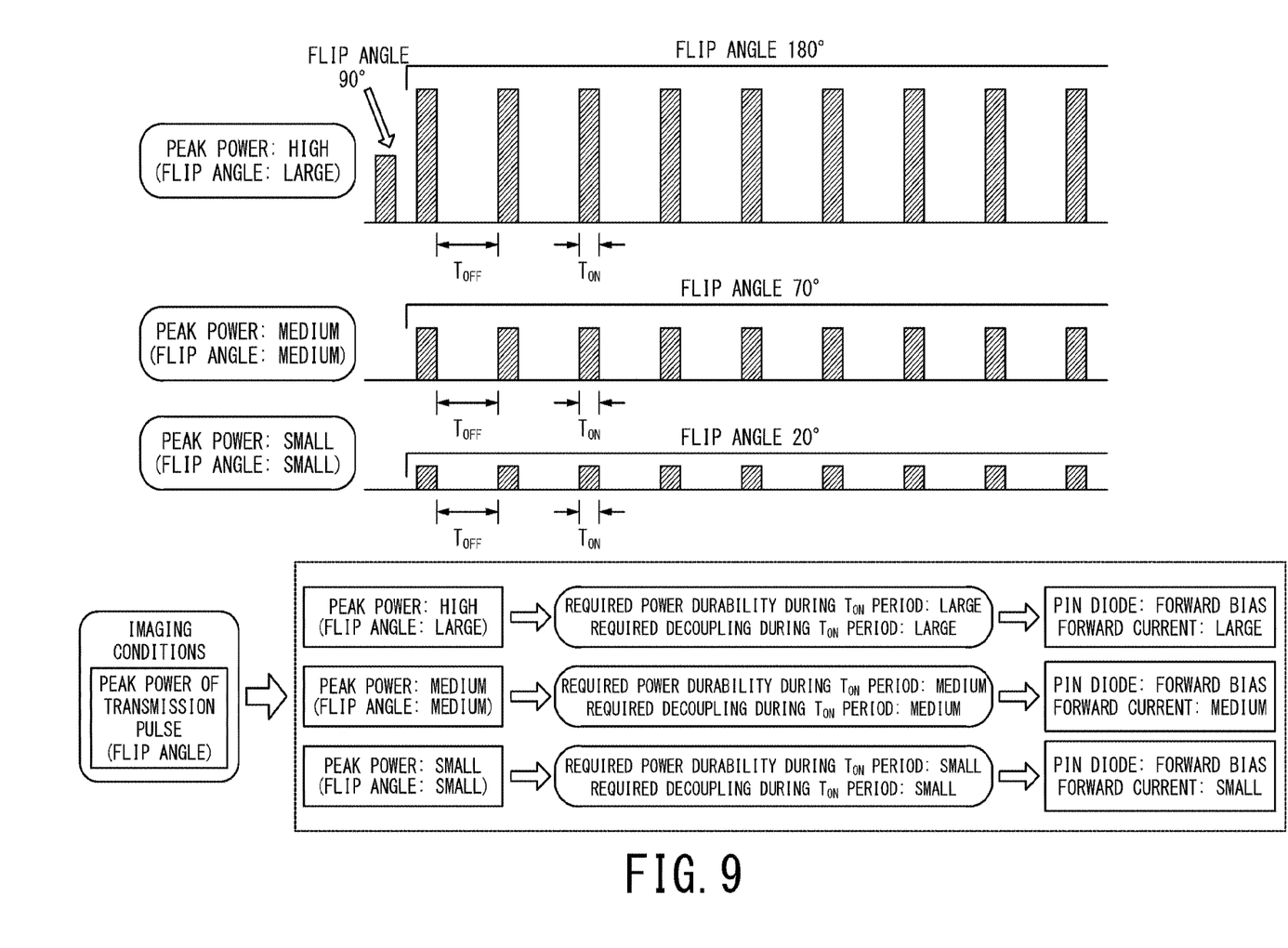
FIG. 9 is a schematic diagram illustrating a third example of the multistage bias control for a PIN diode.

FIG. 9 illustrates bias control in the third example. In the above-described first and second examples and their modifications, the description has been given of the bias control of each PIN diode D during the reception period between the transmission pulses, i.e., during periods other than the ON period of the transmission pulse.

During the application period of the transmission pulse, from the viewpoint of maximizing the degree of decoupling from the transmission coil (for example, the WB coil 12) to ensure uniformity of the radio-frequency magnetic field and the viewpoint of protecting the electronic components and preamplifiers connected to the coil elements 200, the forward current equal to a predetermined value or larger is applied to the PIN diode D.

In the conventional technology, the forward current value of the PIN diode D is set to the state of having the "large forward" current value in FIG. 4B during the application period of the transmission pulse (i.e., during the $T_{ON}$ period in FIG. 9), regardless of the peak power of the transmission pulse (or the magnitude of the flip angle of the RF pulse).

In the third example shown in FIG. 9, for instance, the sequence controller 34 determines the peak power of the transmission pulse (or the flip angle of the RF pulse) from the selected imaging conditions. The control circuit 310 changes the forward current value of the PIN diode D depending on the peak power of the transmission pulse (or the magnitude of the flip angle of the RF pulse). As is well known, the flip angle of the RF pulse differs depending on the type of pulse sequence and/or the type of imaging method, and the transmission peak power of the RF pulse also differs depending on the flip angle.

For example, in the FSE (fast spin echo) pulse sequence shown in the upper row in FIG. 9, an excitation pulse with a flip angle of 90° is applied, and then a refocusing pulse with a flip angle of 180° (i.e., with high peak power) is applied repeatedly. On the other hand, in the GRE (gradient echo) pulse sequence shown in the middle and lower rows in FIG. 9, the flip angle is set to a value smaller than 90°, for example, 70° or 20°.

The transmission peak power of the RF pulse with a flip angle of 70° is lower than the transmission peak power of the RF pulse with a flip angle of 180°. Thus, the required power durability of electronic components such as the PIN diode D and the required decoupling degree during the $T_{ON}$ period of the RF pulse with a flip angle of 70° may be smaller than those during the $T_{ON}$ period of the RF pulse with a flip angle of 180°. That is, during the $T_{ON}$ period of the RF pulse with a flip angle of 70°, the forward current of the PIN diode D can be set to a current value smaller than that during the $T_{ON}$ period of the RF pulse with a flip angle of 180°. For example, the forward current value can be set to the state of having the "medium" forward current value shown in FIG. 4C, and the power consumption of the PIN diode D can be reduced.

Further, the transmission peak power of the RF pulse with a flip angle of 20° is lower than the transmission peak power of the RF pulse with a flip angle of 70°. Hence, the required power durability of electronic components such as the PIN diode D and the required decoupling degree during the $T_{ON}$ period of the RF pulse with a flip angle of 20° may be smaller than those during the $T_{ON}$ period of the RF pulse with a flip angle of 70°. Thus, during the $T_{ON}$ period of the RF pulse with a flip angle of 20°, the forward current of the PIN diode D can be set to a current value smaller than that during the $T_{ON}$ period of the RF pulse with a flip angle of 70°. For example, the forward current value can be set to the state of having the "small" forward current value shown in FIG. 4D, and the power consumption of the PIN diode D can be further reduced.

According to the MRI apparatus of at least one embodiment described above, the power consumption of the PIN diode(s) included in the RF coil can be suppressed.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An MRI apparatus comprising:
   a transmission circuit configured to apply a transmission pulse to an object;
   at least one radio frequency (RF) coil configured to include an active trap circuit provided with a PIN diode, and to receive a magnetic resonance signal from the object;
   a power supply circuit configured to apply a reverse bias voltage and a forward bias voltage to the PIN diode, and to apply multiple values of a forward current when the forward bias voltage is applied to the PIN diode; and
   a control circuit configured to control the power supply circuit in such a manner that the power supply circuit sets the forward current to the multiple values, depending on imaging conditions.

2. The MRI apparatus according to claim 1, wherein the at least one RF coil includes one or a plurality of coil elements.

3. The MRI apparatus according to claim 2, wherein:
   the active trap circuit is provided in each of the one or a plurality of coil elements; and
   the active trap circuit is configured to be able to change degree of decoupling between the RF coil and other RF coil, or degree of decoupling between the coil element and other coil element, depending on a value of the forward current applied to the PIN diode.

4. The MRI apparatus according to claim 3, wherein:
   the at least one RF coil comprises a plurality of RF coils disposed around the object;
   during application period of the transmission pulse, the control circuit controls the power supply circuit to maximize decoupling degree and set the forward current of the PIN diode to a predetermined first value or larger to protect electronic components connected to the coil element; and
   during non-application period of the transmission pulse, the control circuit controls the power supply circuit to enable a first RF coil, which correspond to a body part to be imaged among the plurality of RF coils, to receive the magnetic resonance signal by applying the reverse bias voltage to the PIN diode of the coil element in the first RF coil,
   while the control circuit controls the power supply circuit such that decoupling degree of the coil element of a second RF coil, which does not correspond to the body part to be imaged among the plurality of RF coils, becomes lower than decoupling degree during the application period of the transmission pulse, by applying the forward current of a second value, which is smaller than the predetermined first value, to the PIN diode of the coil element of the second RF coil.

5. The MRI apparatus according to claim 4, wherein the control circuit is configured to control the power supply circuit in such a manner that the second value of the forward current decreases as distance between the first RF coil and the second RF coil increases.

6. The MRI apparatus according to claim 4, wherein:
   the first RF coil is a head coil; and
   the second RF coil is at least one of a body coil and a spine coil.

7. The MRI apparatus according to claim 2, wherein:
   the at least one RF coil includes at least one first coil element corresponding to an imaging region of the object and at least one second coil element corresponding to a region outside the imaging region;
   during application period of the transmission pulse, the control circuit controls the power supply circuit to maximize decoupling degree and set the forward current of the PIN diode to a predetermined first value or larger to protect electronic components connected to the coil element; and
   during non-application period of the transmission pulse, the control circuit controls the power supply circuit to enables the at least one first coil element to receive the magnetic resonance signal by applying the reverse bias voltage to the PIN diode of the at least one first coil element, while the control circuit controls the power supply circuit such that decoupling degree of the at least one second coil element becomes lower than decoupling degree during the application period of the transmission pulse by applying the forward current of a second value, which is smaller than the predetermined first value, to the PIN diode of the at least one second coil element.

8. The MRI apparatus according to claim 7, wherein the control circuit is configured to control the power supply circuit in such a manner that the second value of the forward current decreases as distance between the at least one first coil element and the at least one second coil element increases.

9. The MRI apparatus according to claim 1, wherein the control circuit is configured to control the power supply circuit during application period of the transmission pulse in such a manner that value of the forward current applied to the PIN diode differs depending on a peak power value of the transmission pulse.

10. The MRI apparatus according to claim 9, wherein the control circuit is configured to control the power supply circuit in such a manner that the forward current applied to the PIN diode becomes smaller as the peak power value of the transmission pulse becomes smaller.

* * * * *